(12) United States Patent
Lee et al.

(10) Patent No.: US 11,954,601 B2
(45) Date of Patent: Apr. 9, 2024

(54) METHOD FOR STORING AND UTILIZING GENOME AND GENOMIC INFORMATION

(71) Applicant: Yun Kyung Lee, Gyeonggi-do (KR)

(72) Inventors: Yun Kyung Lee, Gyeonggi-do (KR); Yoo Jin Lee, Gyeonggi-do (KR); Yeong Woo Lee, Gyeonggi-do (KR)

(73) Assignee: Yun Kyung Lee (KR)

( * ) Notice: Subject to any disclaimer, the term of this patent is extended or adjusted under 35 U.S.C. 154(b) by 632 days.

(21) Appl. No.: 17/260,513

(22) PCT Filed: Jul. 16, 2019

(86) PCT No.: PCT/KR2019/008777
§ 371 (c)(1),
(2) Date: Jan. 14, 2021

(87) PCT Pub. No.: WO2020/017869
PCT Pub. Date: Jan. 23, 2020

(65) Prior Publication Data
US 2021/0271982 A1  Sep. 2, 2021

(30) Foreign Application Priority Data
Jul. 17, 2018  (KR) ........................ 10-2018-0083035

(51) Int. Cl.
*G06F 7/00*  (2006.01)
*G06F 16/00*  (2019.01)
(Continued)

(52) U.S. Cl.
CPC ......... *G06N 3/123* (2013.01); *G06F 16/2365* (2019.01); *H04L 9/3247* (2013.01)

(58) Field of Classification Search
CPC .... G06F 16/2365; G06N 3/123; H04L 9/3247
(Continued)

(56) References Cited

U.S. PATENT DOCUMENTS

2015/0213079 A1* 7/2015 Shukla ................ G06F 21/6263
707/687
2019/0179801 A1* 6/2019 Jang ...................... G06F 16/137

FOREIGN PATENT DOCUMENTS

KR  10-2003-0030690 A  4/2003
KR  10-2004-0051748 A  6/2004
(Continued)

OTHER PUBLICATIONS

International Search Report for corresponding International application No. PCT/KR2019/008777; dated Oct. 29, 2019 (5 pages).

*Primary Examiner* — Tuan A Pham
(74) *Attorney, Agent, or Firm* — Mendelsohn Dunleavy, P.C (57) ABSTRACT

Disclosed is a method of storing, in a distributed manner, genomic information in a plurality of nodes, each containing a block chain composed of blocks connected to each other, retrieving at least one piece of the stored genomic information, and acquiring a genomic material corresponding to the retrieved genomic information from a genomic material storage unit that stores genomic materials, each genomic material containing a genome and an artificial nucleic acid sequence. The method includes (1) storing, by each node, genomic information, (2) retrieving, by at least one of the nodes, specific genomic information, and (3) performing authentication.

10 Claims, 9 Drawing Sheets

(51) Int. Cl.
    *G06F 16/23*       (2019.01)
    *G06N 3/123*      (2023.01)
    *H04L 9/32*        (2006.01)

(58) Field of Classification Search
    USPC .................................................. 707/706–770
    See application file for complete search history.

(56) References Cited

FOREIGN PATENT DOCUMENTS

| | | | |
|---|---|---|---|
| KR | 10-2013-0114294 A | 10/2013 | |
| KR | 10-2018-0067183 A | 6/2018 | |
| KR | 10-1868589 B1 | 6/2018 | |

\* cited by examiner

METHOD FOR STORING AND UTILIZING GENOME AND GENOMIC INFORMATION

TECHNICAL FIELD

The present invention relates to a method of storing and using genomes and genomic information, the method being based on encryption technology for storing, distributing, and reprocessing information. More particularly, the present invention relates to a technology for inducing various industrial fields using genomes to adopt a direct-to-customer (DTC) system and to share genomes or genomic information of individuals by enabling persistent authentication of individuals on the basis of encryption of an artificial nucleic acid sequence at the time of preserving and distributing genomes of individuals and by constructing a system for securely and reliably storing, distributing, providing, and reprocessing genomic information using cryptographic technology such as block chain technology.

BACKGROUND ART

Conventionally, in order to study the genome of a living body or corpse, scientists must collect the genome by requesting an individual who has the genome or a specific institution that possesses the genome of many individuals. However, in this case, the types and amounts of genomes that can be obtained are limited, and only institutions or companies which are rich or famous can obtain genomes for their study. Accordingly, the access of general researchers to genome and genomic information is restricted, resulting in a waste of resources and being an obstacle to in-depth research of genomes.

On the other hand, it happens that data from genome analysis are sold to commercial organizations with the genome donor unknowing of the situation or unrewarded for provision of the genome. Therefore, distribution of genome-related profits was improper and security and storage of information derived from genome analysis were inefficient.

Regarding the preservation of genomes, the genomes are stored in the form of DNA, tissue, or blood extracted from each donor, and a bank that classifies individuals (i.e., donors) by a specific sequence (base sequence information) of each individual. In the case of human genome preservation, constructing a bank that possesses the results of genome sequence analysis for all populations per country has been pursued. However, a gene preservation bank per country has not yet been established due to imperfection in preservation technology, security technology for personal information, costs, and only genome preservation conservation banks for studying diseases and traits of individuals have been sporadically established.

To memorialize the deceased, a tomb in which a body or ashes of a body is buried is used. However, tombs have become a burden in terms of environment and costs. In order to solve this problem, the concept of a genomic grave is necessary. According to the concept, the ultimate thing humanity leaves should not be in the form of corpses or burned ash but should be genomic resources.

In this regard, in order to preserve the genome of each individual and distribute it as research resources, an identification method of using external identification tags or labels is mainly used. However, such identification tags or labels are likely to be incorrectly recorded or erroneously attached. In addition, the method cannot support persistent authentication of individuals and is inconvenient in writing information about genomes.

DISCLOSURE

Technical Problem

An objective of the present invention is to provide a method of preserving and utilizing genomic information, in which genome or genomic information is not monopolized by a single party, can be shared by the public, and can be authenticated.

Technical Solution

In order to accomplish the objective of the present invention, there is provided a method of distributing and storing genomic information in a plurality of nodes each including a block chain in which multiple blocks are connected, retrieving at least one item of the genomic information that is stored, and acquiring a genomic material corresponding to the retrieved genomic information from a genomic-material storage unit that stores genomic materials each containing a genome and an artificial nucleic acid sequence, the method including: (1) storing, by each node, genomic information; (2) retrieving, by a search node that is at least one of the nodes, genomic information; and (3) authenticating, wherein the (1) storing step includes (1a) storing the genomic information, (1b) storing location information of each of the nodes, (1c) creating, after the genomic information is stored, a transaction including the stored genomic information and owner information that is location information of a node in which the genomic information is stored, and transmitting the transaction to a specific node of the multiple nodes, and (1d) receiving the transaction from the specific node of the multiple nodes, transmitting a block hash value and a nonce value to the other nodes when a block for the received transaction is created earliest, and creating a block, when receiving a block hash value and a nonce value from a certain node, using the block hash value and the nonce value that are received and connecting the generated block to a block chain, wherein the (2) retrieving step includes (2a) reading the nonce value on each block of the block chain when search information is input, and generating a hash value using the nonce value that is read from the block, the search information that is input, and the location information of the multiple nodes, (2b) determining whether the generated hash value matches with the block hash value of the block on which the nonce value is stored, and (2c) determining that when there is a block having a block hash value that matches with the generated hash value, a node having the location information as an owner, and wherein the (3) authenticating step includes: (3a) receiving authentication information of the owner from the relevant node and (3b) authenticating the genome by comparing the authentication information and the artificial nucleic acid sequence contained in the genomic material stored in the genomic material storage unit.

Advantageous Effects

In the genomic information preservation and utilization method according to the present invention, access to genomic information is allowed after the location of the owner of a target genome is obtained through block chain search. Therefore, the present invention prevents genomes or genomic information from being monopolized by a specific party but enables genomes or genomic information to be shared by the public, thereby contributing to the advancement of genetic research.

In addition, in the genomic information preservation and utilization method according to the present invention, access to a genome is allowed only when authentication information is obtained from the owner of the information of the genome, it is possible to prevent the use of the genome by unauthorized persons.

In addition, in the genomic information preservation and utilization method according to the present invention, a block hash value of a block chain includes genomic information and owner information. Therefore, other users can easily find the location of the genomic information.

In addition, in the genomic information preservation and utilization method according to the present invention, reliability is guaranteed in the process of creating a block chain. Therefore, security integrity is guaranteed through digital signature-based authentication, non-repudiation, and message digest for block hash generation.

BEST MODE

Hereinafter, a system and method for preserving and utilizing genome and genomic information on the basis of a block chain, according to a preferred embodiment of the present invention, will be described in detail with reference to the accompanying drawings.

In the present specification, a genome may be obtained from a living individual or a corpse. The concept of a genome used herein covers not only genomic DNA such as nuclear DNA, whole genomic DNA, and partial genomic DNA extracted from tissue or blood, and fetal DNA contained in blood of a pregnant woman but also genomic DNA such as nuclear DNA, whole genomic DNA, and partial genomic DNA of a specific cell group extracted from specific cells selected from the group consisting of somatic cells, reproductive cells, tumor cells, microbes, and infected cells of other organisms. The genome is a substance such as cDNA or mRNA that is the basis for sequencing and is extracted with a technology developed to study genomic DNA. However, the category or definition of the genome is not limited to genome that is defined based on currently available technology.

In addition, in the present specification, the genomic information includes at least one item selected from among trait information, pathological information, medical information, genome sequence information, genome experiment analysis data information, data mining analysis data information showing relationship between genome and trait or disease, data information extracted through comparison with an existing genome database, any observable phenotype required to study genomes and relevant phenotypes, and phenotypes of various measured data. Genomic sequence information includes cDNA sequence, mRNA sequence, and/or expression profiles, epigenetic data, protein data, whole genome data, methylation data, metabolite data, microbiome data, human sequence data, genotype data from PCR, genotype data from DNA microarrays, genotype data from total genome sequencing, genotype data from whole genome sequencing, genotype data from gene sequencing, karyotype data, pre-implantation genetic testing data, embryo or fetal non-invasive prenatal genetic testing data, etc. The scope of such data is not limited and can be obtained through methods well known in the art.

Figure 1:
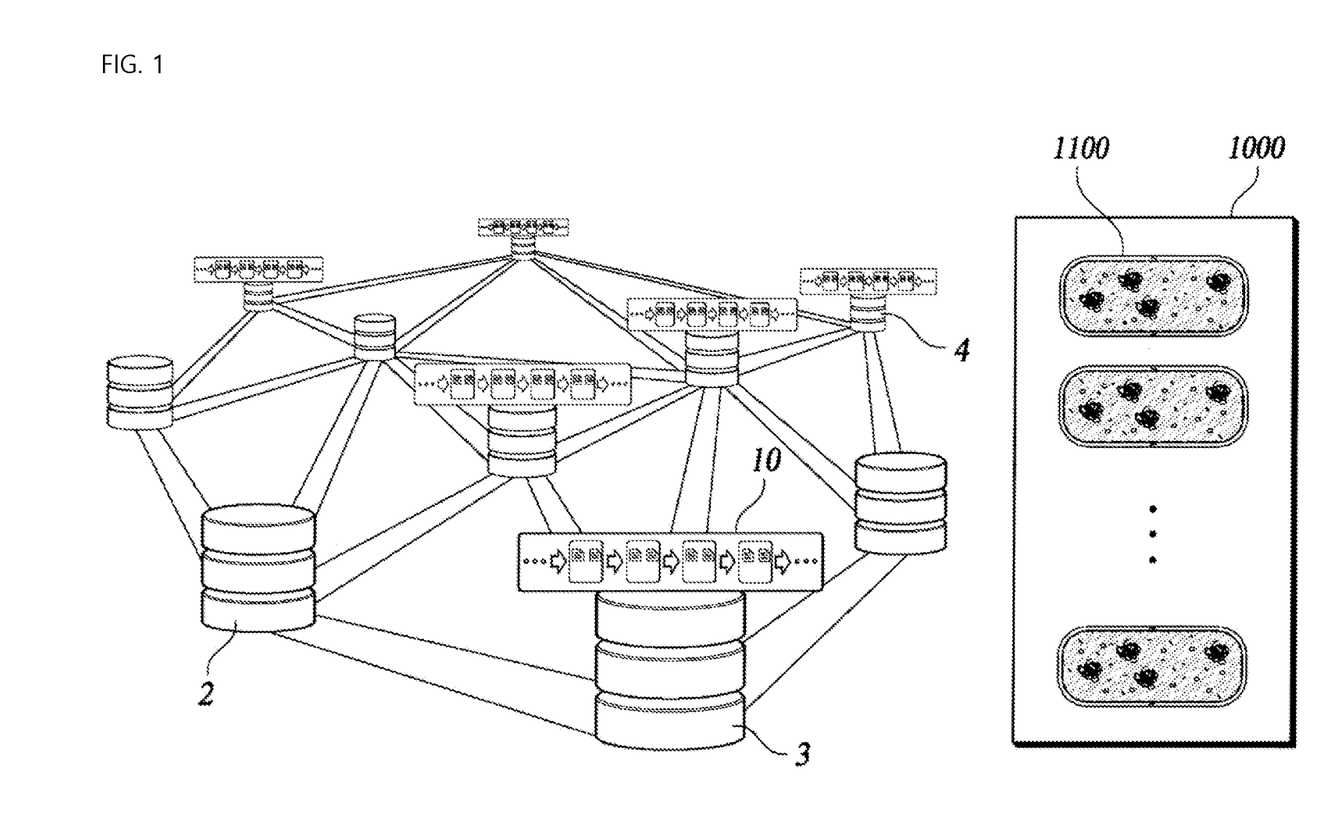
FIG. 1 is a block diagram showing the overall construction of a block chain-based genomic information management system according to one embodiment of the present invention.

FIG. 1 is a diagram illustrating the overall construction of a block chain-based genomic information management system according to one embodiment of the present invention.

Referring to FIG. 1, a genomic information management system 1 according to one embodiment of the present invention is a system for managing and searching for genomic information stored in a plurality of nodes using a block chain. The genomic information management system 1 includes a genome storage unit 1000 and a plurality of nodes 2, 3, 4, . . . , and n.

The genome storage unit 1000 stores genomic materials of a plurality of individuals. Each genomic material includes a genome (genomic DNA) and an artificial nucleic acid sequence. The genomic material may be provided, for example, in the form of a capsule. When the genome storage unit 1000 receives a request for access to a specific genome, the genome storage unit 1000 performs an authentication process using an artificial nucleic acid sequence corresponding to the specific genome and provides or does not provide genomic DNA according to the authentication result. The genomic material stored in the genome storage unit 1000 may be a genomic material taken from a living body or a dead body. When the genomic material of a dead body is stored, the genome storage unit 1000 may function as a genome grave.

Hereinafter, a method of setting an artificial nucleic acid sequence and a method of performing authentication will be described in detail.

DNA or RNA which is the basic unit of information according to the present invention is a substance in which the basic structures of a nucleic acid are linked by a phosphodiester bond and is the same as that is commonly defined in the field of genetic engineering. Nucleic acids are linked like a chain by a phosphodiester binding method to form DNA and RNA. In the structure of nucleic acids, a total of 5 types of compounds can be bound to the base-binding portion. DNA is composed of four types of bases including adenine (A), thymine (T), guanine (G), and cytosine (C) according to the bound compounds and RNA is composed of four types of bases including adenine (A), uracil (U), guanine (G), and cytosine (C). DNA and RNA are distinguished from each other according to which group between —H or —OH is bonded to carbon 2 of the ring structure in FIG. 1A. In vivo, in the form of DNA or RNA, specific amino acids are expressed by three combinations of four types of bases, and proteins are formed by specific combinations of such amino acids. For reference, there are cases in which one type of base is present in two or more compounds. In addition, the nucleic acid sequence is formed by a phosphodiether binding method which is a method of binding bases existing in nature.

There are three ways to match and set the sequence combinations and the information units, for example, as described below.

According to a first setting method, a series of information units is set according to the number of repetitions of one or more bases (sequence units) within a certain allowable count as shown in Table 1. A specific base combination is set as a marker indicating the binding of sequence combinations.

TABLE 1

| Sequence combination | Information unit |
|---|---|
| A | 1 |
| AA | 2 |
| AAA | 3 |
| C | 4 |
| CC | 5 |
| CCC | 6 |
| T | 7 |
| TT | 8 |
| TTT | 9 |
| G | 0 |
| ATG | Binding marker |

[Sequence units are A, T, C, and G]

Table 1 shows an embodiment of a method of setting a specific information unit to an artificial combination of bases and of expressing value information using the setting method. As shown in Table 1, the used bases are A, C, T, and G, and an allowable repetition count is set to 3. ATG is used as a binding marker. ATG as a binding marker provides a direction of base analysis during sequencing and can be used as an indicator that indicates whether the direction of base analysis is correct. For example, when the details of analysis include a sequence combination of GTA, the base analysis should be interpreted in reverse. As shown in Table 1, when expressing the value information "1480632" which is a portion of the resident registration number, the sequence combinations "A", "C", and "TT" are used to indicate the information units "1", "4", "8", respectively, and the binding marker "ATG" is used to verify an appropriate binding form. Therefore, when expressing specific information data "1480632" after setting a series of information units with each arbitrary combination of sequence units, if their nucleic acid sequences are configured in advance, the value information can be easily identified.

Value information: 1 4 8 0 6 3 2

Nucleic acid sequence: A ATG C ATG TT ATG G ATG CCC ATG AAA ATG AA

According to a second setting method, as shown in Table 2 and Table 3, a specific base (sequence unit) is used as an initiation marker and/or a termination marker of a sequence combination, and information units are sequentially set according to a repetition count or an arbitrary combination of one or more bases of the other bases.

Table 2 shows another embodiment of a method of setting a specific information unit to an artificial combination of bases and of expressing value information using the setting method.

TABLE 2

| Sequence combination | Information unit |
|---|---|
| AT | 1 |
| AAT | 2 |
| AAAT | 3 |
| AAAAT | 4 |
| AAAAAT | 5 |
| CT | 6 |
| CCT | 7 |
| CCCT | 8 |
| CCCCT | 9 |
| CCCCCT | 0 |
| T | Termination marker |

[Sequence units are A, C, and T]

As shown in Table 2, T is the terminating marker of a sequence combination, A and C are the repeating sequence units of the sequence combination, and an allowable repetition count is to 5. When the information data "1480632" which is a rear portion of a resident registration number is encrypted in the manner shown in Table 2, the encrypted information data is shown below.

Value information: 1 4 8 0 6 3 2

Nucleic acid sequence: AT AAAAT CCCT CCCCCT CT AAAT AAT

In addition, as shown in Table 3, A is the initiation marker of a sequence combination, and combinations of two bases of A, T, C, and G are set as sequence combinations. When the information data of "1480632" is encrypted in the manner shown in Table 3, the encrypted information data is shown below.

TABLE 3

| Sequence combination | Information unit |
|---|---|
| ACC | 1 |
| ACT | 2 |
| ACG | 3 |
| ATC | 4 |
| ATT | 5 |
| ATG | 6 |
| AGC | 7 |
| AGT | 8 |
| AGG | 9 |
| AAA | 0 |
| AT | Initiation marker |

[Sequence units are A, C, T, and G]

Value information: 1 4 8 0 6 3 2
Nucleic acid sequence: ACC ATC AGT AAA ATG ACG ACT According to a third method, as shown in Table 4, a specific information unit is set to a combination of two or more bases, and value information is set with the specific combinations.

Table 4 shows another embodiment of a method of setting a specific information unit to an artificial combination of bases and of expressing information data using the setting method. As shown in Table 4, three bases are combined in the order of a first base, a second base, and a third base to represent one information unit (alphabet). Information units are indicated by A to Z in Table 4. For example, a sequence combination of "ATT" is created by combining a first base of A, a second base of T, and a third base of T, and the information unit "K" is assigned for the sequence combination. In order to examine whether a nucleic acid sequence contains perfect information, a sequence combination of "CCC" is set as a terminating marker. On the other hand, in order to indicate the completeness of a nucleic acid sequence, the sequence combination "CCC" may be used as an initiation marker. In some cases, the sequence combination "CCC" is used as both of an initiation marker and a termination marker. When the information data is "JONG IL LEE", encryption for this is performed as follows.

TABLE 4

| First base | Second base | | | Third base |
| --- | --- | --- | --- | --- |
| | A | T | C | |
| A | A | J | S | A |
| | B | K | T | T |
| | C | L | U | C |
| T | D | M | V | A |
| | E | N | W | T |
| | F | O | X | C |
| C | G | P | Y | A |
| | H | Q | Z | T |
| | I | R | Termination marker | C |

[Sequence units are A, T, and C]

Value information: J O N G I L L E E
Nucleic acid sequence: ATA TTC TTT CAA CAC ATC ATC TAT TAT CCC The artificial nucleic acid sequence of the present invention is formed by selecting any one of the above-exemplified methods of mapping sequence combinations to information units. However, the methods described above are only some exemplary ways among numerous ways to map sequence combinations to information units.

Such an artificial nucleic acid sequence can be authenticated in reverse to the method described above. For example, when receiving authentication information, the genomic material storage unit 1000 obtains value information from a nucleic acid sequence by applying the method in reverse and performs authentication by comparing the obtained value information with the authentication information. When it is confirmed that the provider of the authentication information is a legitimate right holder, the genome corresponding to the authentication information which is the nucleic acid sequence can be provided to the provider of the authentication information.

Figure 2:
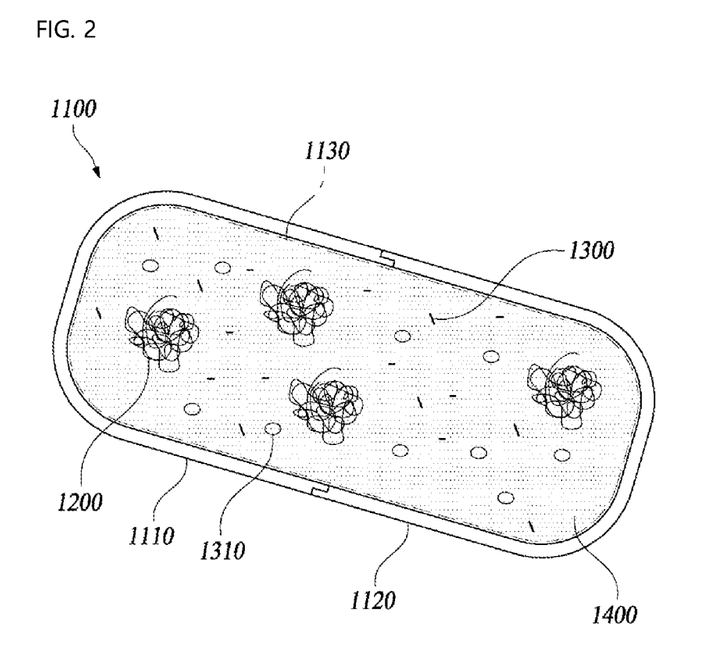
FIG. 2 is a diagram showing a capsule in which a genome is preserved, according to one embodiment of the present invention.

FIG. 2 is a diagram showing a capsule 1100 in which a genomic material is preserved, according to one embodiment of the present invention. The genomic material storage unit 1000 stores multiple capsules 1100 generated for respective objects.

Referring to FIG. 2, the capsule 1100 is composed of a left capsule 1110 and a right capsule 1120 that are made of a material that is not deformed by heat and mechanical external stress and that can be separated from and combined with each other. In some cases, the capsule may further include an inner skin 1130 made of a heat-resistant material that allows the contents to be more safely held and protected from external heat or a waterproof material that facilitates storage and protection. Since the capsule 1100 contains a large number of specific human genomic DNA 1200 and an artificial nucleic acid sequence DNA 1300 which are dispersed in a solution 1400, although some genomic DNAs 1200 or artificial nucleic acid sequence DNAs 1300 are damaged, authentication can be performed by analyzing the remaining DNAs.

On the other hand, as shown in FIG. 2, the artificial nucleic acid sequence may be provided in the capsule 1100 in a state 1310 of being bound to the vector. As described above, since the artificial nucleic acid sequence DNA 1300 consists of a relatively much smaller number of bases than the genomic DNA 1200, it can be simply analyzed within a short time.

The above-described capsule form is only an example, and it will be apparent to a person skilled in the art that it can be modified into one of various forms and configurations.

Referring back to FIG. 1, a plurality of nodes 2, 3, 4, . . . , and n provide genomic materials to the genomic material storage unit 1000, store genomic information corresponding to the respective genomic materials, and search for genomic information. When an individual provides a genomic material to the genomic material storage unit 1000 and directly stores genomic information corresponding to the genomic material in his or her computer, the individual's computer corresponds to one of the plurality of nodes 2, 3, 4, . . . , and n. Alternatively, an individual may provide a genomic material to the genomic material storage unit 1000 and make a request for management of genomic information to a company that specializes in managing genomic information. In this case, the genomic information management company may correspond to one of the plurality of nodes 2, 3, 4, . . . , and n. Further alternatively, the nodes 2, 3, 4, . . . , and n may correspond to medical-related genome analysts or individuals, organizations, companies, etc. who need genomes for analysis.

Figure 3:
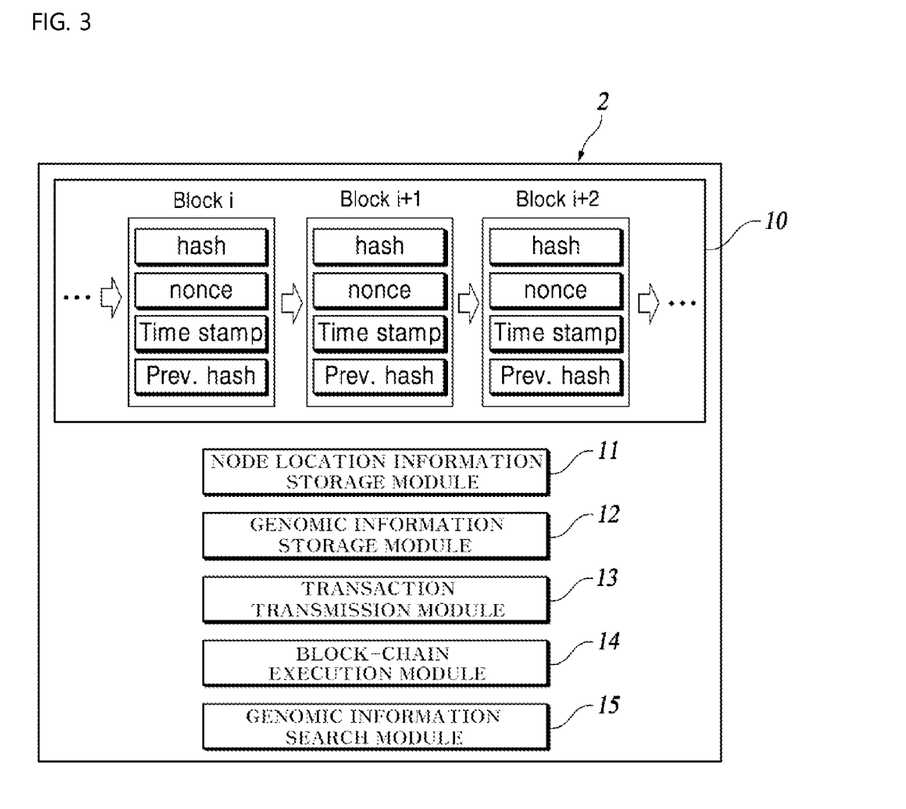
FIG. 3 is a block diagram showing the structure of each node in the genomic information management system according to the present invention.

FIG. 3 is a block diagram showing the structure of each node in the genomic information management system according to the present invention.

Referring to FIG. 3, each of the nodes 2, 3, 4, . . . , n is equipped with a block chain 10, a node location information storage module 11, a genomic information storage module 12, a transaction transmission module 13, a block chain execution module 14, and a genomic information search module 15.

The block chain 10 is formed by connecting a plurality of blocks in a chain shape. In this regard, referring to FIG. 3, each block of the block chain contains a hash value of a current block, a nonce value, a hash value of a previous block, and a time stamp. The hash value and the nonce value are values obtained by using a preset hash function on the basis of the genomic information and the IP address and port number of the owner. Since each of the blocks in the block chain contain not only their own block hash value but also the block hash value of the previous block, each block of the block chain is connected to each other like a chain.

The node location information storage module 11 stores location information of each of the nodes 2, 3, 4, . . . , and n. Such location information may be, for example, the IP address and the port number of each node. Every node is equipped with the node location information storage module 11.

The genomic information storage module 12 is a memory area in which genomic information is stored, and each node pre-designates a folder for storing genomic information to be shared with other nodes. With the system according to the present invention, it is possible to provide an information sharing platform through which all nodes can share genomic information stored in their genomic information storage module 12. Each of the nodes 2, 3, 4, . . . , n provides a genomic material to the genomic material storage unit 1000 of FIG. 1, and then stores genomic information corresponding to the provided genomic material in the genomic information storage module 12 thereof. Alternatively, each of the nodes 2, 3, 4, . . . , n locates a node in which the desired genomic information is stored from among the nodes 2, 3, 4, . . . , and n, receives authentication information from the found node (i.e., owner node), receives a genomic information from the genomic material storage unit 1000 on the basis of the received authentication information, generates new genomic information (hereinafter, referred to as secondary genomic information) on the basis of the analysis results, and stores the generated genomic information (i.e., secondary genomic information) in the genomic information storage module 12 thereof. The genomic information or the secondary genomic information may include at least one item selected from among expression traits such as an individual's appearance or medical history, a treatment history, and genetic analysis information. Hereinafter, the term "genomic information" is defined as a concept including the secondary genomic information.

When genomic information is stored in a predetermined folder of the genome information storage module 12, the transaction transmission module 13 generates a transaction including the stored genomic information, owner information, and digital signature and transfers the generated transaction to other nodes having their block chain. In addition, when secondary genomic information is stored in a predetermined folder of the genome information storage module 12, the transaction transmission module 13 generates a second transaction including the stored secondary genomic information, owner information, and digital signature and transfers the second transaction to other nodes having their block chain. Hereinafter, the term "transaction" is used to include the second transaction. In this specification, for convenience of description, a node that has transmitted a transaction and a second transaction is referred to as a "transaction transmitting node". Owner information may include an IP address and a port number of a node in which genomic information is stored.

The genomic information is included in the transaction in the form of ASCII code, and the owner's IP address and port number are included in the transaction in the form of decimal numbers.

When the block chain execution module 14 receives a transaction from another node having a block chain, the block chain execution module 14 creates a block for the received transaction and connects the block to the block chain thereof, thereby expanding the block chain. In this specification, for convenience of description, a node that has received a transaction from a transaction transmitting node is referred to as a "transaction receiving node". Hereinafter, the operation of the block chain execution module 14 will be described in more detail.

When the block chain execution module 14 receives a transaction from another node, it executes a proof-of-work to create a block hash value necessary to create a block by itself. The proof of work is an operation of creating a hexadecimal block hash value that satisfies a predetermined number of '0's by calculating a random nonce value with the received transaction using a preset hash function. The system according to the present invention uses the SHA 256 hash function. Alternatively, a different hash function may be used. The reason for the proof of work is to make it impossible to know which node of the nodes participating in creating the block chain will generate a block, thereby preventing a malicious node from being aware which node will generate a current block and preventing the malicious node from attacking the node that will generate the block. For example, the height of the block chain of bitcoin is 417453, and the number of '0's in this block hash value is 17. The bitcoin adjusts a block generation difficulty by increasing the number of '0's. The block generation difficulty is set in a manner of taking the number of '0's when generating one block every 10 minutes with a system currently having the highest CPU or GPU performance.

When a transaction receiving node successfully performs the proof of work earliest among all of the transaction receiving nodes, the block chain execution module 14 thereof finds a block hash value and a random nonce value, creates a block using the values, and transmits the values to all of the nodes. In this specification, for convenience of description, a node that first succeeds in the proof of work among the transaction receiving nodes is referred to as a "proof-of-work success node".

When the block chain execution module 14 receives the block hash value and the nonce value from the proof-of-work success node, the block chain execution module 14 verifies the transaction, the received block hash value, and the received nonce value with a validity verification algorithm, creates a new block using the received block hash value and the received nonce value when the verification is successfully completed, and connects the generated block to the block chain.

The genomic information search module 15 searches genomic information and owner information stored in each of the nodes using the block chain 10 and the node location information storage module 11.

When the search information is input, the genomic information search module 15 reads the nonce value of each block stored in the block chain, generates a block hash value using the nonce value, the search information, and the IP address and port number of each node of the nodes included in an IP list, and examines whether the generated block hash value matches with the block hash value of the block in which the nonce value is contained. When there is a block having a block hash value that matches the generated block hash, the node having the IP address and the port number is determined to be the owner, and the node is requested to provide authentication information corresponding to an artificial nucleic acid sequence stored in the genomic information storage unit 1000. The genomic information storage unit 1000 confirms that the person presenting the authentication information has appropriate authority to use the requested genome by comparing the authentication information with the artificial nucleic acid sequence, and provides the requested genome to the person who presented the authentication information. When there is no block having a block hash value matching the generated block hash value, it is determined that there is no corresponding data.

Meanwhile, in the system according to the present invention, when receiving a transaction from one of the other nodes having a block chain, the block chain execution module 14 generates a block for the received transaction and connects the generated block to the block chain.

Hereinafter, in the block chain-based genomic information management system having the above-described configuration, a method of managing and searching genomic information at each node will be described in more detail.

Figure 4:
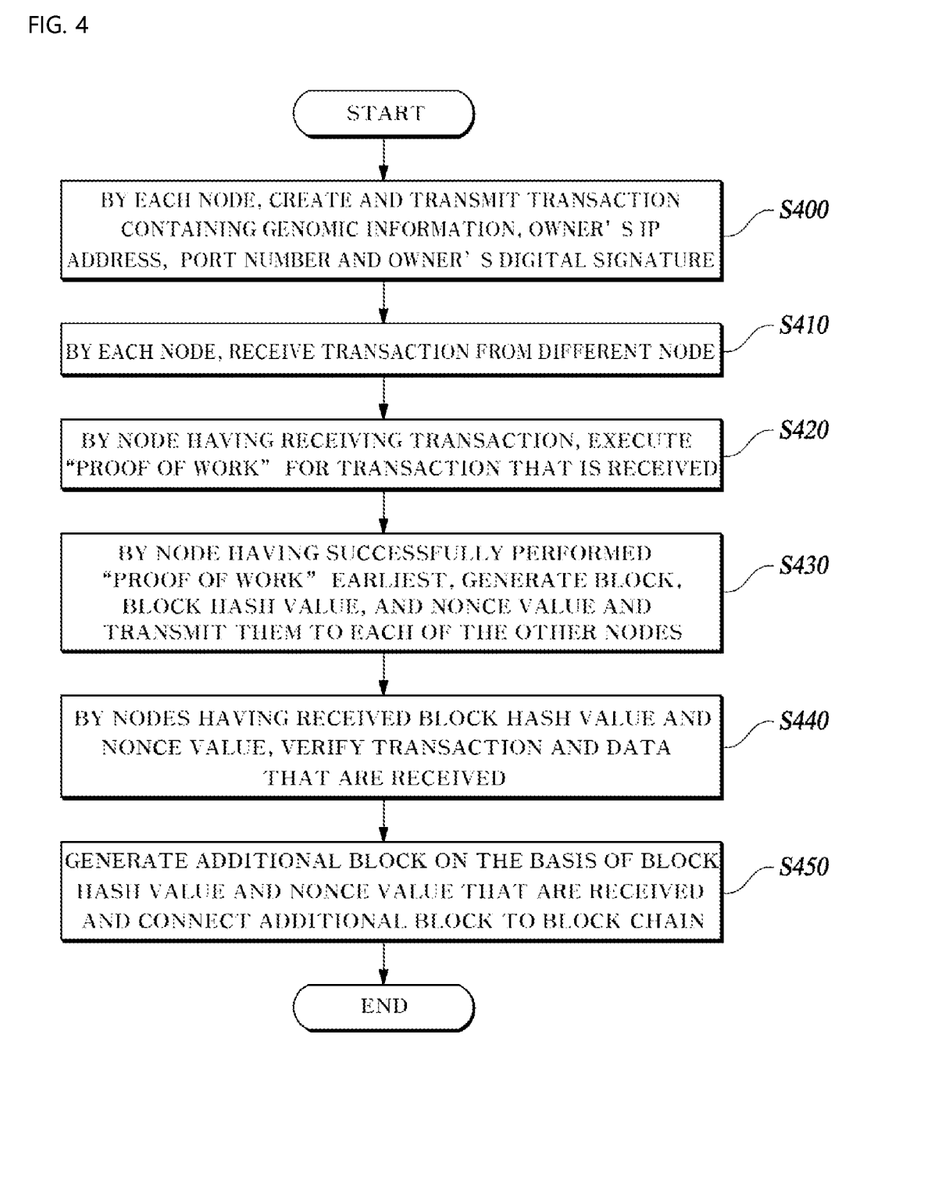
FIG. 4 is a flowchart sequentially illustrating a process of connecting blocks including genomic information and owner information to a block chain performed by each node in the genomic information management system according to one embodiment of the present invention.

FIG. 4 is a flowchart illustrating a process in which each node connects a block containing genomic information and owner information to a block chain in a genomic information management system according to an embodiment of the present invention. Referring to FIG. 4, the process in which each node connects a block containing genomic information and owner information to a block chain will be described in detail below.

Each node has a block chain and IP list and pre-designates an area for storing genomic information to be shared with other nodes in the genome information storage module thereof.

First, each node generates and stores genomic information in the preset area using the transaction transmission module thereof, creates a transaction including the genome information, the IP address and port number of the node of the owner of the genomic information, and digital signature of the owner, and transmits the generated transaction to other nodes (S400).

The other nodes receive a transaction from the transaction transmitting node (S410).

The transaction receiving nodes perform the proof-of-work in order to generate a block hash value necessary to generate a block for the received transaction using the block chain execution module (S420).

Among the transaction receiving nodes, the node that first succeeded in the proof-of-work finds a block hash value and a random nonce value using the block chain execution module, creates a block on the basis of the block hash value and the nonce value, notifies the other blocks that it has generated the block, and transmits the block hash value and the nonce value for the block to the other nodes (S430).

The other nodes that have received the block hash value and the nonce value from the proof-of-work success node verify the transaction and the received block hash value and nonce value using a validity verification algorithm (S440), create their new block on the basis of the received block has value and nonce value when the validation is successfully completed, and connect the newly generated block to the block chain (S450).

Figure 5:
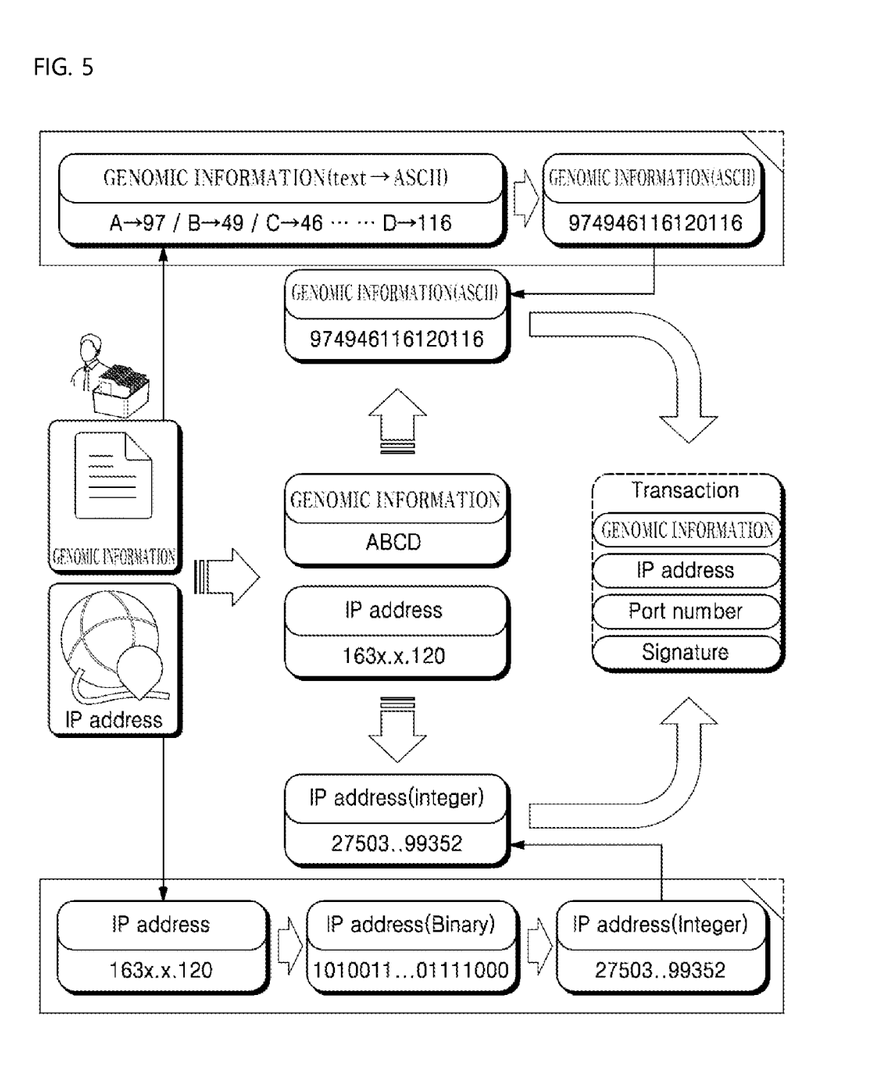
FIG. 5 is a block diagram illustrating a process of generating a transaction by a transaction transmission module of each node in a genomic information management system according to a preferred embodiment of the present invention.

FIG. 5 is a configuration diagram illustrating a process in which a transaction transmission module of each node creates a transaction in a genomic information management system according to a preferred embodiment of the present invention.

Referring to FIG. 5, the owner stores genomic information in a predetermined area. In this case, the genomic information includes various items such as height, weight, eyesight, respiratory treatment history, and hypertension treatment history, and each field for storing a corresponding item is filled with numbers or letters corresponding to the information. It is desirable that the generated genomic information is expressed in the form of ASCII code which results from conversion of letters into numbers and in which codes are arranged to form a simple string. In addition, the IP address is first converted into a binary code and then into a decimal code. Through this process, a transaction is created along with the extracted genomic information, the owner's IP address and port number, and the owner's digital signature.

Figure 6:
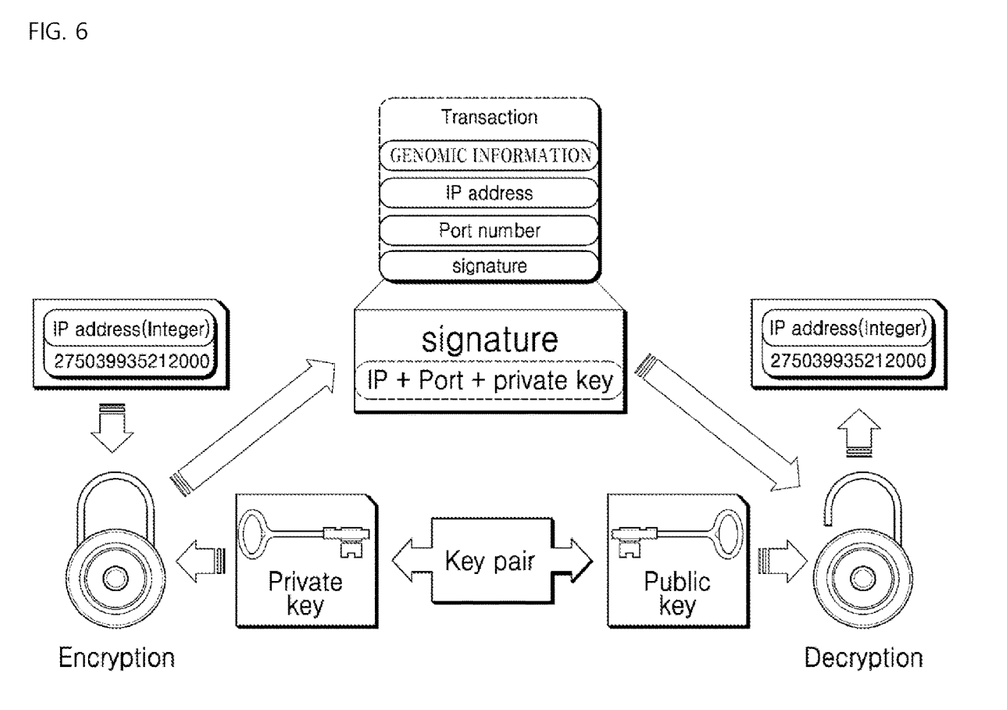
FIG. 6 is a conceptual diagram illustrating encryption and decryption algorithms for digital signature in the genomic information management system according to the preferred embodiment of the present invention.

FIG. 6 is a conceptual diagram illustrating an encryption and decryption algorithm for digital signature in a genomic information management system according to a preferred embodiment of the present invention.

Referring to FIG. 6, in the system according to the present invention, when a transaction transmitting node which is the node of a data owner transmits a transaction, the transaction transmitting node generates digital signature using a private key and inserts the digital signature into the transaction to be transmitted. A transaction receiving node decodes the digital signature included in the received transaction using a public key and checks whether the IP address and port number of the owner who sent the transaction match with the IP address and port number included in the transaction.

The system according to the present invention generates digital signature using a private key and a public key. The cryptographic theory used for generation of the digital signature is ECDSA. The IP address of the transaction transmitting node and the port number of the owner to use TCP socket communication are arranged, and are then encrypted with the private key to generate digital signature. The digital signature is attached to the transaction, and the transaction with which the public key generated with the use of ECDSA is enclosed is transmitted to other nodes. The transaction receiving node verifies the transaction by decrypting the transaction with the enclosed public key and checking whether the output result is True or False. By preventing spoofing by verifying the digital signature, it is possible to prevent any malicious node from sending an invalid transaction, thereby preventing the information in the invalid transaction from being used to generate a block.

Figure 7:
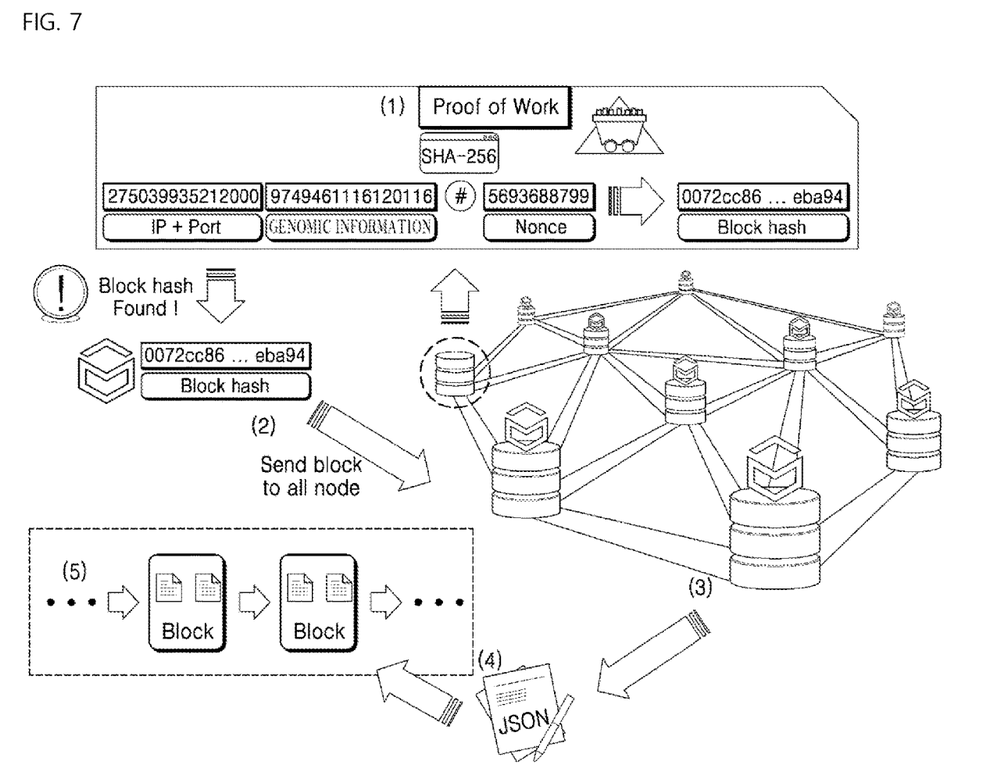
FIG. 7 is a conceptual diagram illustrating a process in which a transaction receiving node generates and transmits a block hash value through proof of work in the genomic information management system according to a preferred embodiment of the present invention.

FIG. 7 is a conceptual diagram illustrating a process in which a transaction receiving node generates a block hash value through proof of work and transmits the block hash value in a genomic information management system according to a preferred embodiment of the present invention.

Referring to FIG. 7, a required level of block generation difficulty for a Bitcoin blockchain is set such that the number of '0's in a block hash is 17, and the difficulty level is set accordingly. Unlike the existing block chains in which a block contains multiple transactions, a block in the system according to the invention contains only one transaction. That is, one piece of genomic information and one piece of owner information are provided in one block. A block has is made with the use of only this information in advance. Thus, search information and owner information can be checked through block hash analysis when data is searched later. The IP, port number, and genomic information received through the transaction are listed to apply a hash algorithm, a nonce value is randomly generated, and a block hash is generated using the SHA256 hash algorithm (Step 1). The nonce value is continuously changed until a hash value with more than 17 zeros which is a preset reference zero count is found. When a hash satisfying the condition is found, it is accepted as a block hash. The block hash value and the nonce value that are generated by a random node are transmitted to all of the nodes participating in the block chain (Step 2), and each of the receiving nodes performs verification of the transaction by analyzing the block hash value and the nonce value that are received (Step 3). Since each node has all pieces of transaction information required for creation of a block, the IP address, port number, and genomic information which are included in the transaction information are listed, and the SHA256 hash algorithm is executed on the basis of the received nonce value. When the output hash value of the execution of the SHA256 hash algorithm is identical to the received block hash value, the node determines that the contents of the transaction have not been altered. In this way, the creation of a block based on information from a malicious node can be prevented. The blocks that have undergone validation are stored in the form of Json files (Step 4) and are then connected to the block chain (Step 5).

Figure 8:
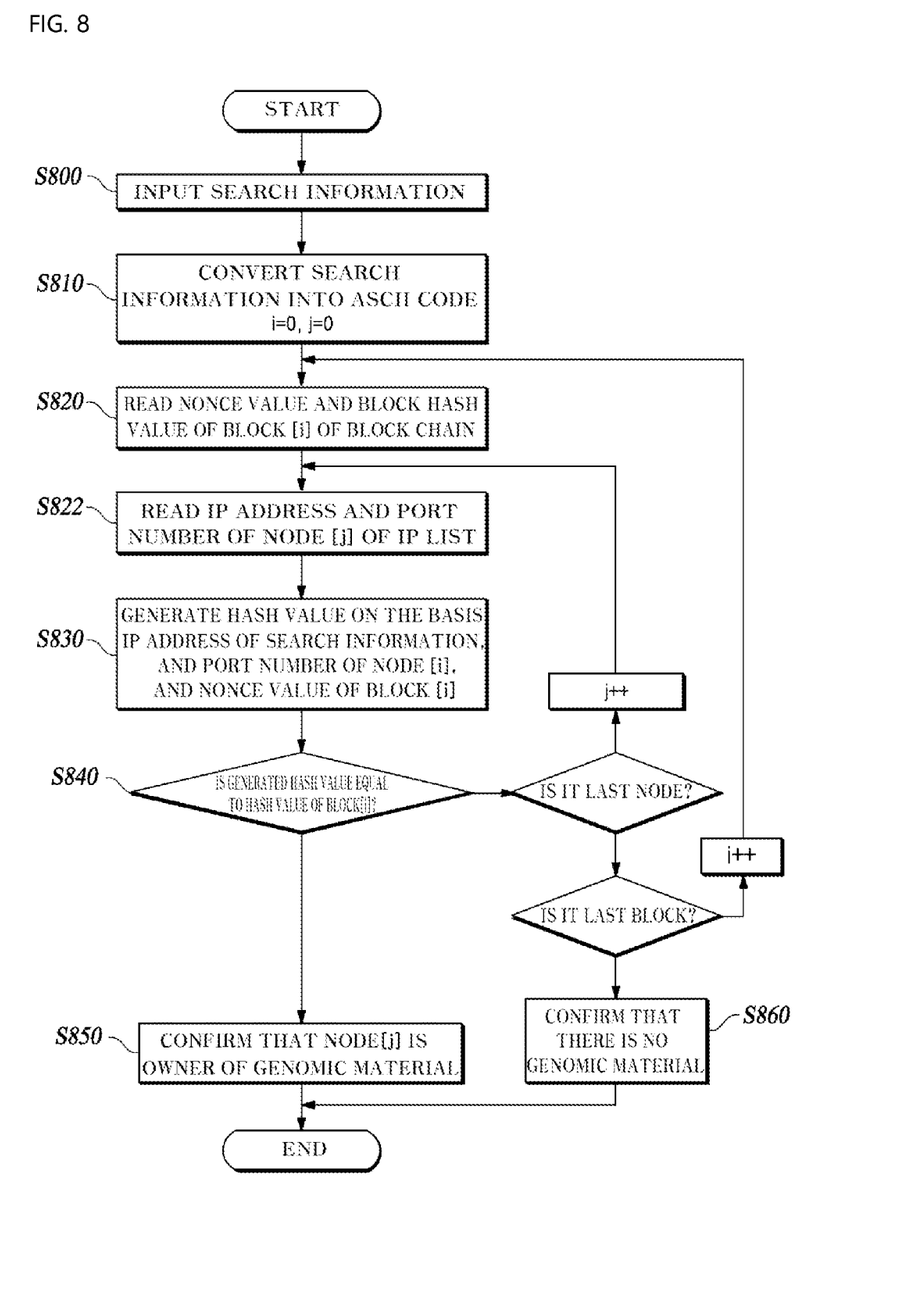
FIG. 8 is a flowchart illustrating an operation of a genomic information search module of each node in the genomic information management system according to the preferred embodiment of the present invention.
Figure 9:
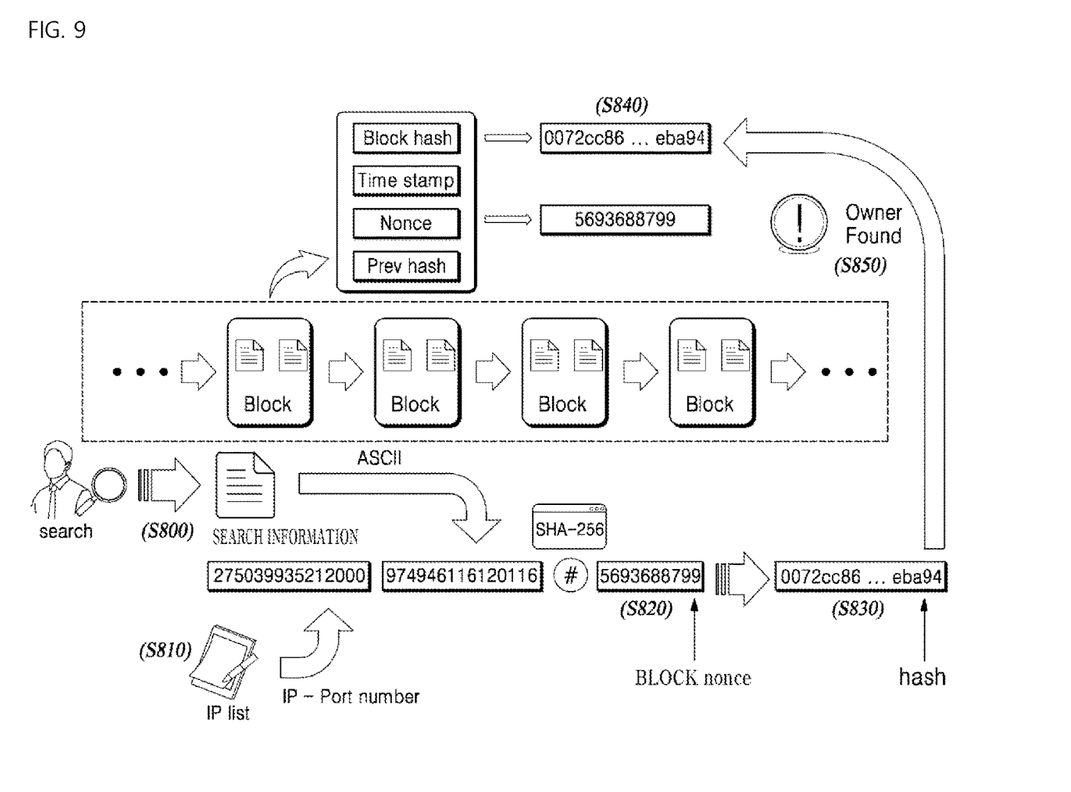
FIG. 9 is a conceptual diagram illustrating a process of identifying an owner after searching for genomic information stored in a block chain using the genomic information search module of each node.

FIG. 8 is a flowchart showing the operation of a genomic information search module of each node in a genomic information management system according to a preferred embodiment of the present invention, and FIG. 9 is a conceptual diagram illustrating a process in which each node checks owner information after searching for genomic information stored in a block chain using a genomic information search module.

Referring to FIGS. 8 and 9, when a user inputs search information (a) (S800), the search information is converted into ASCII code and then information of the IP address and port number of each node in the node location information storage module 11 and the ASCII code are listed together (S810). The block chain 10 stored in the Json file format is read to read the nonce value (S820), the SHA256 hash algorithm is applied to the nonce value that is read and the listed information to obtain a hash value (S830), and it is checked whether the obtained hash value matches the block hash value of the Json file (S840). One Json block is opened to find the hash value and the nonce value using the IP addresses and port numbers of all nodes included in the IP list. If there is no matching hash value in the block, the next block is opened and the same operation is performed on the opened block. When a hash value that matches the hash value of the block is found, it is possible to confirm that the node with the IP address and port number is the owner of the data that is searched (S850). When the searched genomic information does not exist in the block chain, a message of "not found" is returned (S860).

As described above, the genomic information management system according to the present invention finds the IP address and port information of an owner of a requested genome by searching a block chain for the hash of the genome, thereby implementing a platform capable of providing a list of sharable genome information. In addition, when the owner information of the genome information is found from the block chain, the search node requests the owner node to provide authentication information corresponding to the genome information, and the owner node transmits the authentication information to allow the search node to perform authentication in the genomic material storage unit. Accordingly, the genomic material storage unit can provide the genome corresponding to the authentication information to the search node (i.e., person who performed the authentication).

Here, the owner node may transmit the authentication information to the searched node only when a specific condition is satisfied. For example, the conditions may include a case where the research institute or analyst corresponding to the search node conducts research in a field designated by the owner node or a case where the search node pays a desired cost. Accordingly, the owner of the genome may not be alienated but be involved in the process of distributing genetic resources.

Thereafter, the search node having received authentication information from the owner node may analyze the genome obtained from the genomic material storage unit and generate genome analysis information (i.e., secondary genomic information).

The genomic analysis information is statistically significant data obtained through comparative analysis in which the obtained genome is compared with information stored in various databases constructed for biomedical research or through numerical or text data mining of genome information through the various databases. Examples of the database constructed for biomedical research are described below and newly constructed databases will also be included. The examples are listed below.

NCBI databases (including but not being limited to GenBank and Entrez) or other public or private databases such as DNA Data Bank of Japan (National Institute of Genetics), European Nucleotide Archive (European Institute of Bioinformatics) Ensembl, UniProt, Swiss-Prot, Proteomics Identifications Database, European Protein Information Bank, Japanese Protein Information Bank, Biomolecular Interaction Network Database, Reactome, mGen, PathogenPortal, SOURCE, MetaBase, BioGraph, Bioinformatic Harvester, Enzyme Portal, Max Planck Institute, Illumina that includes and is not limited to Illuminas Laboratories and/or BAS-ESPACE, Life Technologies, Complete Genomics, Pacific Biosciences, Affymetrix, Agilent, Sequenom, Arrayit Corporation, Laboratory Corporation of America, Quest Diagnostics, Empire Genomics, Expression Analysis, GeneDx, Gene by Gene, Natera, Ambry Genetics, National Geographic, CoriellInstitute for Medical Research, Kaiser Permanente, databases of governments, databases of researchers, databases of universities, databases of laboratories, laboratory genetic testing equipment, devices that perform genetic testing (for example sequencers and/or lab-on-chip), databases of medical institutions, databases of medical institutions, health-related databases, databases of health insurance companies, databases, databases of public enterprises, and genomic information analysis databases owned or controlled by BioPhysical Corporation, Spectracell Laboratories, Health Diagnostic Laboratory Inc., Knome, Counsyl, Ancestry.com, Family Tree DNA, Match.com, eHarmony, okCupid, Drugs.com, Human Gene Mutation Database, Online MendelianInheritance in Man, SNPedia, Wikipedia, Facebook, Myspace, LinkedIn, Google (including but being not limited to Internet search history, click history, GooglePlus databases, Amazon, Apple, Yahoo!, Instagram, Pinterest, Twitter, European Molecular Biology Laboratory, Asia Pacific BioInformatics Network, Beijing Genomics Institute, Healthcare.gov, United States Department of Health and Human Services, The Centers for Medicare and Medicaid Services, United States Veterans Affairs, Calico, DNANexus, Pathway Genomics, i-gene, personal computers, personal phones, personal tablet devices, personal electronic devices, Genotek, bio-logis, Genelex, Lumigenix, Spiral Genetics, databases of medical workers, electronic medical records, electronic health records, Xcode Life Sciences, Riken Genesis, Personalis, MapMyGenome, and/or 23andMe.

The search node stores secondary genomic information in the same manner as a method of storing genomic information, creates a block, and connects the block to a block chain. Therefore, it is possible for the public to have access to secondary genomic information derived from the primary genomic information as well as the primary genomic information, resulting in contribution to a breakthrough in genetics and related industries.

The genomic information management system and the method using the same system according to the present invention can solve the problem of consuming a large storage capacity by storing genomic information and owner information using a block chain and sharing necessary data. The data sharing is performed in a manner to first find the location and owner of the data through a block chain search and to request provision of information from the owner of the data.

Accordingly, each individual can reduce the effort or cost required to manufacture and manage a grave by storing a genomic material in a genome grave corresponding to the genomic material storage unit 1000 and can allow the genomic material to be shared by third parties.

In addition, a party who performs genome analysis can easily find genomic information of a necessary genomic material and obtain a genomic material by contacting the owner of the corresponding genomic material. Accordingly, while genomic materials have been conventionally monopolized by a specific company or institution, the present invention enables genomic materials to be openly accessible, thereby contributing to development of medical and genetic industries.

Although the present invention has been described with reference to preferred embodiments, the preferred embodiments are presented to describe the technical spirit of the present invention only for illustrative purposes and are not intended to restrict the scope of the present invention. In addition, those skilled in the art will appreciate that various modifications and changes are possible, without departing from the essential characteristics of the present invention. In addition, differences related to these modifications and applications should be construed as falling within the scope of the present invention defined in the appended claims.

The invention claimed is:

1. A method of (i) distributing and storing genomic information in a plurality of connected nodes that constitute a block chain, (ii) retrieving at least one item of the genomic information that is stored in the block chain, and (iii) authenticating the retrieved genomic information for acquiring a genomic material corresponding to the retrieved genomic information from a genomic-material storage unit that stores genomic materials each containing a genome and an artificial nucleic acid sequence, the method comprising:
   (1) storing, by each node, genomic information;
   (2) retrieving, by a search node that is at least one of the nodes, genomic information; and
   (3) authenticating,
   wherein the (1) storing step includes (1a) storing the genomic information, (1b) storing location information of each of the nodes, (1c) creating, after the genomic information is stored, a transaction including the stored genomic information and owner information that is location information of a node in which the genomic information is stored, and transmitting the transaction to a specific node of the multiple nodes, and (1d) receiving the transaction from the specific node of the multiple nodes, transmitting a block hash value and a nonce value to the other nodes when a block for the received transaction is created earliest, and creating a block, when receiving a block hash value and a nonce value from a certain node, using the block hash value and the nonce value that are received and connecting the generated block to a block chain,
   the (2) retrieving step includes (2a) reading the nonce value on each block of the block chain when search information is input, and generating a hash value using the nonce value that is read from the block, the search information that is input, and the location information of the multiple nodes, (2b) determining whether the generated hash value matches with the block hash value of the block on which the nonce value is stored, and (2c) determining that when there is a block having a block hash value that matches with the generated hash value, a node having the location information as an owner, and the (3) authenticating step includes: (3a) receiving authentication information of the owner from the relevant node and (3b) authenticating the genome contained in the genomic material stored in the genomic material storage unit by comparing the authentication information and value information, wherein:
   the artificial nucleic acid sequence includes sequential bindings of DNA or RNA bases;
   the value information is a sequential binding of information units of numbers or letters; and
   the value information is obtained by interpreting the artificial nucleic acid sequence corresponding to the genome in step (3b) by using a correspondence relationship between sequential bindings of the DNA or RNA bases included in the artificial nucleic acid sequence and the information units constituting the value information.

2. The method according to claim 1, wherein the (3b) authentication step comprises:
   (3b-1) mapping the information units of numbers or letters to artificial combinations of DNA or RNA bases;
   (3b-2) expressing the value information that can be expressed by sequential binding of the information units according to the correspondence relationship as an artificial nucleic acid sequence that is the form of sequential binding of DNA or RNA bases; and
   (3b-3) interpreting the artificial nucleic acid sequence as the value information according to the correspondence relationship, and comparing the value information resulting from analysis with the authentication information that is input when the authentication information is input.

3. The method according to claim 2, wherein the value information is name, resident registration number, or unique authentication number.

4. The method according to claim 1, wherein each of the genomic materials is a capsule containing a genome of an object and an artificial nucleic acid sequence connected to a vector.

5. The method according to claim 1, wherein each block of the block chain is generated for the genomic information stored in the multiple nodes, and
   the block hash value of each block is generated by applying a predetermined hash algorithm to genomic information, owner information corresponding to the genomic information, and a nonce value corresponding to the genomic information.

6. The method according to claim 1, wherein the owner information includes an IP address and a port number of a node in which the genomic information is stored.

7. The method according to claim 1, wherein the transaction contains digital signature.

8. The method according to claim 1, wherein the genomic information is an individual's phenotypic trait, an individual's treatment history, or both.

9. The method according to claim 1, wherein the (3a) authentication information reception step includes:
   (3a-1) transmitting, by the node corresponding to the owner, the authentication information to the search node when search node satisfies a predetermined condition; and
   (3a-2) receiving, by the search node, the authentication information.

10. The method according to claim 1, further comprising (4) updating the genomic information after the (3) authentication step is performed, wherein the (4) updating step includes:

(4a) generating and storing secondary genomic information on the basis of the genome corresponding to the artificial nucleic acid sequence used in the authentication step;

(4b) creating a second transaction containing the secondary genomic information and second owner information that is location information of a node in which the secondary genomic information is stored after the secondary genomic information is stored, and transmitting the generated second transaction to the other nodes; and (4c) receiving a second transaction from one of the nodes, transmitting a block hash value and a nonce value to the other nodes when generating a block for the received second transaction earliest, generating a block, when receiving a block hash value and a nonce value from one of the nodes, on the basis of the received values, and connecting the generated block to the block chain.

\* \* \* \* \*